United States Patent
Trofast

(10) Patent No.: US 7,179,489 B2
(45) Date of Patent: Feb. 20, 2007

(54) PROCESS FOR PREPARING A PHARMACEUTICAL COMPOSITION CONTAINING AN ACTIVE INGREDIENT AND A MICRONISED CARRIER/DILUENT

(75) Inventor: Eva Trofast, Lund (SE)

(73) Assignee: AstraZeneca AB, Sodertalje (SE)

( * ) Notice: Subject to any disclaimer, the term of this patent is extended or adjusted under 35 U.S.C. 154(b) by 341 days.

(21) Appl. No.: 10/276,458

(22) PCT Filed: May 17, 2001

(86) PCT No.: PCT/SE01/01117

§ 371 (c)(1),
(2), (4) Date: Nov. 18, 2002

(87) PCT Pub. No.: WO01/89491

PCT Pub. Date: Nov. 29, 2001

(65) Prior Publication Data

US 2003/0129245 A1 Jul. 10, 2003

(30) Foreign Application Priority Data

May 19, 2000 (GB) ................... 0012261.4

(51) Int. Cl.
*A61K 9/14* (2006.01)
*A61K 31/16* (2006.01)

(52) U.S. Cl. ............ 424/489; 514/630; 514/951; 514/952

(58) Field of Classification Search ........... 424/46, 424/489, 499; 264/15; 514/630, 826, 951; 141/1, 71, 82; 241/1, 3, 23, 29; 23/313 R
See application file for complete search history.

(56) References Cited

U.S. PATENT DOCUMENTS

| 5,674,860 A | 10/1997 | Carling et al. ............ 514/171 |
| 5,684,199 A | 11/1997 | Francotte ................. 564/261 |
| 5,709,884 A | 1/1998 | Trofast et al. ............ 424/489 |
| 5,795,564 A | 8/1998 | Aberg et al. |
| 5,874,063 A * | 2/1999 | Briggner et al. ............ 424/45 |
| 6,030,604 A | 2/2000 | Trofast .................... 424/46 |
| 2001/0049396 A1* | 12/2001 | Ekstrom ................ 514/727 |

FOREIGN PATENT DOCUMENTS

| WO | WO 95/05805 | 3/1995 |
| WO | WO 98/31351 | 7/1998 |
| WO | WO 99/15182 | 4/1999 |
| WO | WO 00/28979 | 5/2000 |
| WO | WO 01/78693 A2 | 10/2001 |

* cited by examiner

*Primary Examiner*—Frederick Krass
(74) *Attorney, Agent, or Firm*—Fish & Richardson P.C.

(57) ABSTRACT

The invention relates to a stable pharmaceutical composition useful in the treatment of respiratory disorders such as asthma, rhinitis and chronic obstructive pulmonary disease (COPD) and a novel micronization process for manufacturing a stable formulation for formoterol or its enantiomers and a carrier/diluent comprising a carbohydrate such as lactose.

11 Claims, 2 Drawing Sheets

Stability data for formoterol / lactose in Turbuhaler

A= formoterol fumarate dihydrate (0.5%) / lactose monohydrate (99,5%) according to example 1
B= formoterol fumarate dihydrate (0.5%) / lactose monohydrate (99,5%) according to example 2

L = carrier/diluent
F = formoterol
L(C) = coarse particlaes of carrier/diluent
L(M) = small particles of carrier/diluent produced by methods like micronisation, direct precipitation etc.
F(M) = small particles of formoterol produced by methods like micronisation, direct precipitation etc.

US 7,179,489 B2

PROCESS FOR PREPARING A PHARMACEUTICAL COMPOSITION CONTAINING AN ACTIVE INGREDIENT AND A MICRONISED CARRIER/DILUENT

CROSS REFERENCE TO RELATED APPLICATIONS

The present application is a national phase application under 35 U.S.C. Section 371 filed from International Patent Application PCT/SE01/01117, filed 17 May 2001, which claims priority to United Kingdom patent application Serial No. 0012261.4, filed 19 May 2000. The contents of these applications are incorporated herein by reference in their entirety.

FIELD OF INVENTION

The present invention relates to a stable pharmaceutical composition and a novel micronisation process for manufacturing a stable formulation for formoterol or its enatiomers and a carrier/diluent comprising a carbohydrate such as lactose.

BACKGROUND OF THE INVENTION

Stability is one of the most important factors which determines whether a compound or a mixture of compounds can be developed into a therapeutically useful pharmaceutical product. When mixing different ingredients in a pharmaceutical formulation there exists the possibility of interactions taking place between the components. In addition, each component may have different degradation characteristics.

Formoterol is a highly potent and selective β2-agonist with a long duration of action when inhaled. Compared to other β-adrenergic compounds it has a unique chemical structure with a formamido group substituted on the benzene ring. It has two asymmetric carbon atoms in the molecule making four stereoisomers possible. Most studies, clinical and preclinical, appear to have been performed with the fumarate (as dihydrate) of the enantiomeric mixture designed R;R+S;S. The R;R enantiomer is the most potent of the four enantiomers.

The stability profile of the drug formoterol (as fumarate dihydrate) has been evaluated by investigating the influence of variables such as storage time, temperature, relative humidity, light and pH on the content of formoterol and determining the amount of chromatographic impurities. Formoterol (as fumarate dihydrate) has been demonstrated to be stable under long-term storage even at high temperatures and high relative humidities. However, the chemical structure of formoterol makes the molecule prone to chemical degradation when in contact with e.g. a reactive species like an aldehyde or under stress conditions e.g. a milling process.

Potent drugs for administration by inhalation are generally formulated in association with carriers/diluents such as lactose to facilitate accurate dosing from an inhaler. These formulations have generally consisted of coarse particles of a carrier together with fine particles of the drug(s), optionally together with small particles of carrier/diluent, which combination is generally known as an ordered mixture. An alternative to such a formulation is to agglomerate the small particles of the drug(s) and the carrier/diluent to agglomerates.

Formoterol (as fumarate dihydrate) as well as a carbohydrate e.g. lactose (preferably as the monohydrate) are very stable compounds individually, but degradation products are formed when the two compounds are mixed. A mixture of formoterol fumarate dihydrate and lactose monohydrate can be regarded as a three component system composed of formoterol fumarate, lactose and water. By sorption of water a saturated aqueous lactose solution is formed at the surface of the powder mixture. A certain amount of formoterol fumarate dissolves in this aqueous solution and is thereby susceptible to degradation. Therefore, the relative humidity, as well as the storage temperature, will influence the stability of the powder mixture.

It would therefore be desirable to develop a formulation with good stability in spite of the complex mixture of compounds having reactive chemical groups like an amine (formoterol), formamide (formoterol) and a carbohydrate (e.g. lactose). The presence of hydrates (formoterol fumarate dihydrate, lactose monohydrate) will make it even more complex.

DESCRIPTION OF THE INVENTION

In accordance with the present invention, there is provided a process for preparing a pharmaceutical composition comprising, in admixture, an active ingredient which is micronised formoterol or an enantiomer thereof and a micronised carrier/diluent, which process comprises:

1. preparing a mixture of micronised active ingredient and carrier/diluent,
2. followed by addition of further pre-micronised carrier/diluent which is mixed in at low energy, and
3. either subjecting the mixture to agglomeration and spheronisation, or adding coarse carrier/diluent.

The first active ingredient and carrier/diluent can be prepared according to step 1 by micronising the two components together or each can be micronised individually and then combined to give a micronised mixture. Preferably the first active ingredient and carrier/diluent are mixed together and then micronised.

Preferably step 3 involves subjecting the mixture to agglomeration and spheronisation.

Optionally the mixture/ingredients can be conditioned at any suitable stage of the process, such as between steps 1 and 2, and/or the further pre-micronised carrier/diluent can be conditioned at step 2, and/or the mixture can be conditioned between the agglomeration and spheronisation in step 3. Preferably the the mixture/ingredients is conditioned between steps 1 and 2, and the further pre-micronised carrier/diluent is conditioned at step 2.

Conditioning can be carried out according to the procedures described in WO 95/05805 or by selecting the process parameters such as relative humidity in such a way that the final product when submitted to water vapour gives off heat of less than 1.2 joules per gram for the particles having a mean particle size of less than 10 μm as described and measured in U.S. Pat. No. 5,874,063.

By "low energy" is meant mixing at low pressure, preferably below 2 bar, more preferably below 1 bar. Preferably the micronisation as well as the mixing step are carried out in a spiral jet mill.

By "micronised" is meant milling to give a desired particle size or obtaining a desired particle size by any other means for producing small particles such as direct precipitation.

The process of the invention produces compositions having high storage stability in that the decomposition of formoterol in the formulation will be less than 10% when stored in open dishes at 40° C. and 75% relative humidity for 6 months when the content of formoterol is less than about 1.0% (w/w), preferably less than about 0.8% (w/w) and most preferably less than about 0.6% (w/w) in the formulation or, when stored in a dry powder device, a decomposition of less than about 2.5% under the same conditions.

The formoterol can be in the form of a mixture of enantiomers. Preferably the formoterol is in the form of a single enantiomer, preferably the R;R enantiomer. The formoterol can be in the form of the free base, salt or solvate, or a solvate of a salt, preferably the formoterol is in the form of its fumarate dihydrate salt. Other suitable physiologically salts include chloride, bromide, sulphate, phosphate, maleate, tartrate, citrate, benzoate, 4-methoxybenzoate, 2- or 4-hydroxybenzoate, 4-chlorobenzoate, p-toluenesulphonate, benzenesulphonate, ascorbate, acetate, succinate, lactate, glutarate, gluconate, tricaballate, hydroxynapaphthalenecarboxylate or oleate.

Preferably the carrier/diluent is a carbohydrate, more preferably a reducing carbohydrate such as lactose, glucose, galactose, mannose, xylose, maltose, cellobiose, mellibiose, maltotriose (e.g. as monohydrates). More preferably the carrier is lactose, most preferably lactose monohydrate.

As used herein the term micronised carrier/diluent refers to carrier/diluent having a mean particle size of less than about 25 µm, preferably less than about 10 µm, more preferable less than about 5 µm. The term coarse carrier/diluent refers to carrier/diluent having a mean particle size of greater than about 25 µm.

As used herein the term micronised active ingredient means active ingredient having a mean particle size of less than about 10 µm, preferably less than about 5 µm.

The pharmaceutical compositions according to the invention can be used for the treatment or prophylaxis of a respiratory disorder, in particular the treatment or prophylaxis of asthma, rhinitis or COPD.

In a further aspect the invention provides a method of treating a respiratory disorder, in particular asthma, rhinitis or COPD, in a mammal which comprises administering to a patient a pharmaceutical composition as herein defined.

The compositions of the invention can be inhaled from a nebulizer, from a pressurized metered dose inhaler or as a dry powder from a dry powder inhaler e.g. multidose reservoir systems from AstraZeneca (Turbuhaler) or Schering-Plough or from a dry powder inhaler utilizing gelatine, plastic or other capsules, cartridges or blister packs. Doses will be dependent on the severity of the disease and the type of patient.

EXPERIMENTAL SECTION

The invention is illustrated by the following examples which are not intended to limit the scope of the application. In the examples micronisation is carried out such that the particle size range for each of the active components is suitable for administration by inhalation. The determination of the formoterol degradation products was performed by reversed phase liquid chromatography, on a two column system using LiChrospher 60 RP-select B. 5 µm particles with octylsilane as stationary phase. UV-detector at 214 nm. Evaluation was done as area-% since the degradation products were not fully known.

Example 1

The following example is a reference example in which the formulation is prepared in a conventional manner.

Formoterol fumarate dihydrate (26.5 g) and lactose monohydrate (4.97 kg) are mixed for one or two hours in a tumbling mixer. This mixture was micronised in a spiral jet mill in order to attain a particle size suitable for inhalation. Micronisation of substances into the low micron range (1–5 µm) may induce disturbances in the crystallinity of the substance. Amorphous areas are introduced, especially at the surfaces of the micronised substance. This morphological change of the substances will increase the sensitivity to humidity and thereby being an potential implement to stability problems. The crystal structure of the substance mixture was restored in a controlled way according to U.S. Pat. No. 5,874,063, or U.S. Pat. No. 5,709,884.

To improve the flowability of the cohesive powder it was spheronised to agglomerates at room temperature at a controlled relative humidity of less than 50%. The micronised and spheronised formoterol fumarate dihydrate/lactose monohydrate formulation according to example 1 was filled in the powder device Turbuhaler (AstraZeneca) and stored for 6 months at 40° C. and 75% relative humidity. Results are shown in FIG. 1(A).

Example 2

Formoterol fumarate dihydrate (0.575 kg) and lactose monohydrate (4.425 kg) were mixed for two to four hours in a tumbling mixer. The mixture was micronised in a spiral jet mill in order to attain a particle size suitable for inhalation. The crystal structure was restored in a controlled way according to U.S. Pat. No. 5,874,063, or U.S. Pat. No. 5,709,884. To part of this mixture (223 g) was added further micronised and conditioned lactose monohydrate (4.77 kg) and the mixture was blended using very low energy in a modified spiral jet mill followed by a spheronisation step to provide agglomerates.

Figure 1:
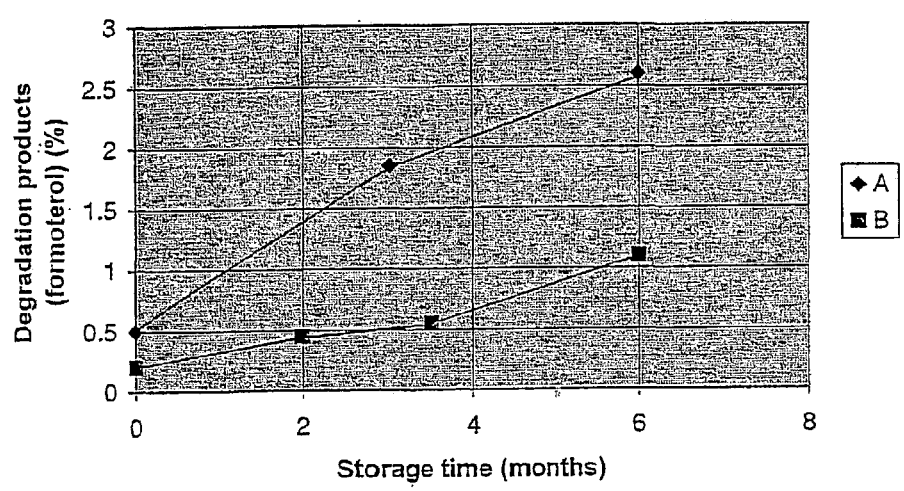
FIG. 1 is a graph illustrating the results of the experiments described in Examples 1 and 2.
Figure 2:
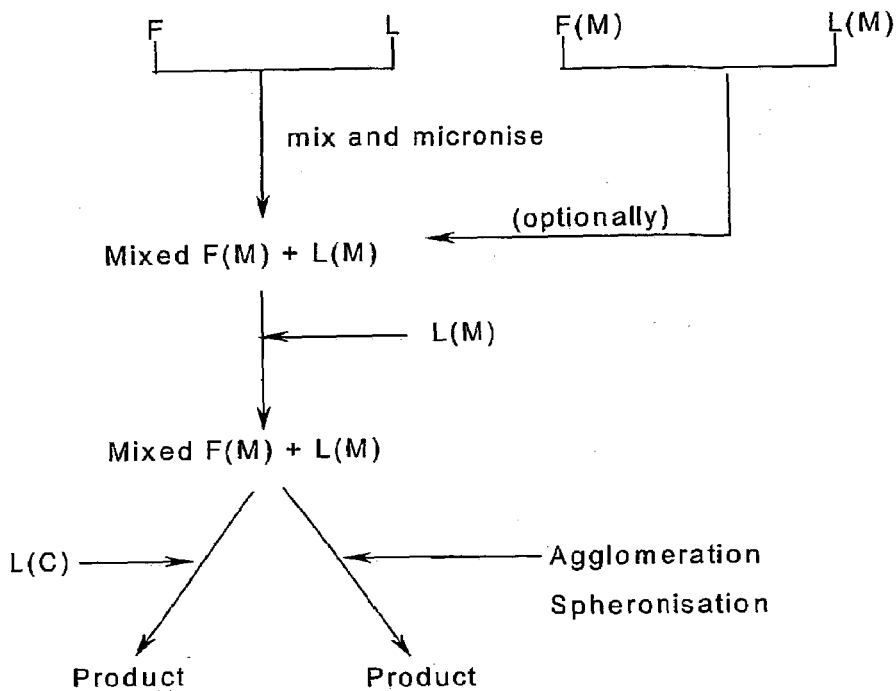
FIG. 2 is a diagram showing the steps of a process according to one embodiment of the invention.

The micronised and spheronised formoterol fumarate dihydrate/lactose monohydrate formulation was filled into the dry powder device Turbuhaler® (AstraZeneca) and stored for 6 months at 40° C. and 75% relative humidity. Results are shown in FIG. 1 (B).

The invention claimed is:
1. A process for preparing a pharmaceutical composition comprising, in admixture, an active ingredient which is micronised formoterol or an enantiomer thereof, optionally in the form of a salt or solvate or a solvate of a salt, and a micronised carrier/diluent, which process comprises
   (a) preparing a mixture of micronised active ingredient and carrier/diluent,
   followed by (b) addition of further pre-micronised carrier/diluent which is mixed in at a pressure of less than 2 bar, and
   (c) either subjecting the mixture to agglomeration and spheronisation, or adding coarse carrier/diluent.
   wherein the pharmaceutical composition exhibits a storage stability such that the decomposition of formoterol on the composition will be less than 10% (w/w) when stored in open dishes at 40° C. and 75% relative humidity for 6 months when the content of formoterol is less than about 1.0% (w/w) in the composition.

2. A process according to claim 1 in which formoterol is in the form of its fumarate dihydrate salt.

3. A process according to claim 1 in which the formoterol is in the form of the single R,R-enantiomer.

4. A process according to any one of claims 1 in which the carrier is a coarse carbohydrate.

5. A process according to any one of claims 1 in which the carrier is lactose.

6. A process according to claim 1 wherein the mixing is performed at a pressure of less than 1 bar.

7. A process according to claim 1 wherein the mixture of the active ingredient and the carrier/diluent is prepared by micronising the active ingredient and the carrier/diluent together.

8. A process according to claim 1 wherein the mixture of the active ingredient and the carrier/diluent is prepared by micronising the active ingredient and the carrier/diluent individually and then combining them to give a micronised mixture.

9. A process according to claim 1 wherein step (c) comprises subjecting the mixture to agglomeration and spheronisation.

10. A process according to claim 1 further comprising conditioning the mixture between steps (a) and (b).

11. A process according to claim 10 further comprising conditioning the mixture again between the agglomeration and spheronisation in step (c).

* * * * *

UNITED STATES PATENT AND TRADEMARK OFFICE
CERTIFICATE OF CORRECTION

| | | |
|---|---|---|
| PATENT NO. | : 7,179,489 B2 | Page 1 of 1 |
| APPLICATION NO. | : 10/276458 | |
| DATED | : February 20, 2007 | |
| INVENTOR(S) | : Eva Trofast | |

It is certified that error appears in the above-identified patent and that said Letters Patent is hereby corrected as shown below:

Col 5, Lines 7 and 9 after "according to" delete "any one of claims" and insert --claim--.

Signed and Sealed this

Seventeenth Day of June, 2008

JON W. DUDAS
*Director of the United States Patent and Trademark Office*